US009567417B1

(12) United States Patent
Czaplewski et al.

(10) Patent No.: US 9,567,417 B1
(45) Date of Patent: Feb. 14, 2017

(54) POLYMERIC MATERIALS HAVING PHTHALATE PLASTICIZERS COVALENTLY BONDED TO A POLYMER CHAIN

(71) Applicant: International Business Machines Corporation, Armonk, NY (US)

(72) Inventors: Sarah K. Czaplewski, Rochester, MN (US); Joseph Kuczynski, North Port, FL (US); Jason T. Wertz, Pleasant Valley, NY (US); Jing Zhang, Poughkeepsie, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 14/871,348

(22) Filed: Sep. 30, 2015

(51) Int. Cl.

| | |
|---|---|
| ***C08F 8/32*** | (2006.01) |
| ***C08J 3/18*** | (2006.01) |
| ***C08F 114/06*** | (2006.01) |
| *C08L 27/24* | (2006.01) |
| *C08L 27/22* | (2006.01) |
| *C08L 27/06* | (2006.01) |

(52) U.S. Cl.
CPC ................ *C08F 114/06* (2013.01); *C08F 8/32* (2013.01); *C08J 3/18* (2013.01); *C08J 2327/06* (2013.01); *C08J 2327/22* (2013.01); *C08J 2327/24* (2013.01); *C08L 27/06* (2013.01); *C08L 27/22* (2013.01); *C08L 27/24* (2013.01)

(58) Field of Classification Search
CPC ............ C08F 8/32; C08J 3/18; C08J 2327/06; C08J 2327/22; C08J 2327/24; C08K 5/17; C08K 5/10; C08K 5/11; C08K 5/12; C08L 27/06; C08L 27/22; C08L 27/24
USPC .......................... 525/331.5, 331.6, 382, 386
See application file for complete search history.

(56) References Cited

U.S. PATENT DOCUMENTS 2,514,185 A * 7/1950 Eberly .................... C08K 5/17 524/252
6,831,121 B2 12/2004 Lee et al.
2015/0112008 A1 4/2015 Patil et al.

FOREIGN PATENT DOCUMENTS

CN 103834128 A 6/2014
CN 104530583 A 4/2015
KR 100850048 B1 8/2008

OTHER PUBLICATIONS

Yang et al., RCE Advances 5 (2015) 16980-16985.*
Earla et al., Macromol. Rapid Commun. 35 (2014) 666-671.*
Navarro et al., Macromolecules 43 (2010) 2377-2391.*
Brookman, R., "Flexible PVC: An Industry Mainstay Pushes the Performance Envelope", Plastics Engineering, Jun. 2002, vol. 58, Issue 6, ISSN: 0091-9578, 5 pages.
Deloach, Joseph, "Dibutyl Terephthalates in Plasticizer and Related Applications", Eastman Chemical Company, IP.com, IP.com No. 000236730, May 13, 2014, 11 pages.
Navarro, et al., "Phthalate Plasticizers Covalently Bound to PVC: Plasticization with Suppressed Migration", American Chemical Society, Macromolecules 2010, vol. 43, pp. 2377-2391.
Earla, A. et al. "Covalently Linked Plasticizers: Triazole Analogues of Phthalate Prepared by Mild Copper-Free 'Click' Reactions with Azide-Functionalized PVC", Macromolecular Rapid Communications, vol. 35, Issue 6, 2014, http://onlinelibrary.wiley.com/doi/10.1002/marc.201300865/abstract, pp. 666-671.
Ehrenberg, R. "Plasticizers Kept from Leaching Out: 'Chemicals of Concern' May be Made Safer", usnews.com, ScienceNews, 2010, http://www.usnews.com/science/articles/2010/03/03/plasticizers-kept-from-leaching-out, 2 pages.

* cited by examiner

*Primary Examiner* — Roberto Rabago

(57) ABSTRACT

In an example, a process of forming a polymeric material is disclosed. The process may include chemically reacting a polyvinyl chloride (PVC) material with a diamine to form a diamine-modified PVC material. The diamine has a chemical formula $(CH_2)_x(NH_2)_2$, where x is not less than 2. The process may also include chemically reacting a halogenated phthalate plasticizer with the diamine-modified PVC material to form a polymeric material having a phthalate plasticizer covalently bonded to a polymer chain.

20 Claims, 2 Drawing Sheets

Figure 1:
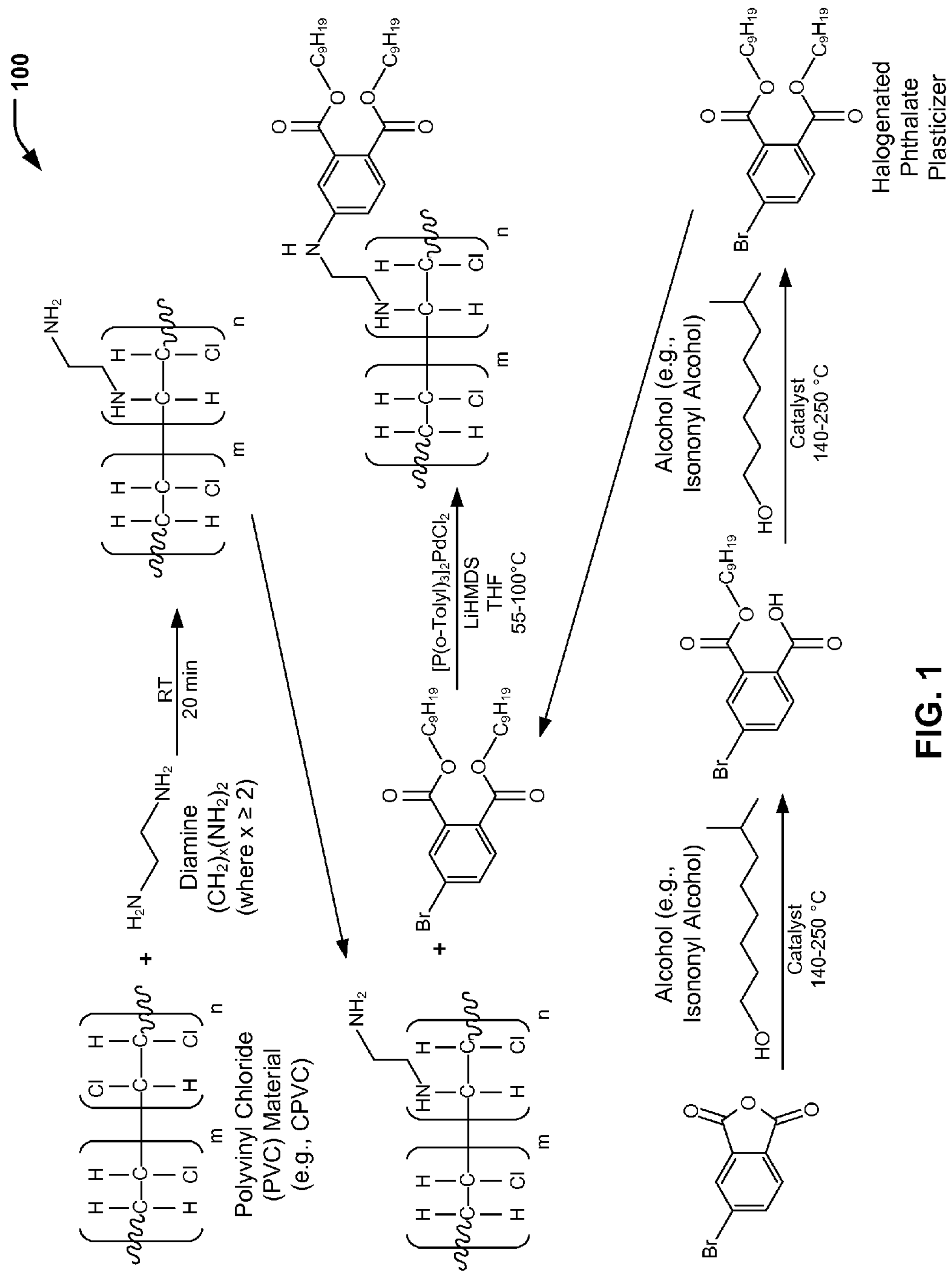

POLYMERIC MATERIALS HAVING PHTHALATE PLASTICIZERS COVALENTLY BONDED TO A POLYMER CHAIN

I. FIELD OF THE DISCLOSURE

The present disclosure relates generally to polymeric materials having phthalate plasticizers covalently bonded to a polymer chain.

II. BACKGROUND

Plasticizers may be used to improve the flexibility of some polymeric materials. As an example, a plasticizer additive may improve the flexibility of a polyvinyl chloride (PVC) material in order to provide a sufficient degree of flexibility to allow the PVC material to be used for a particular application. For example, a plasticizer additive may provide sufficient flexibility to a PVC material to allow the PVC material to be used as an insulating material for wires/cabling of information technology hardware. In some applications, such as immersion cooling of information technology hardware, leach-out of plasticizer additives may result in degradation of the material properties of PVC-insulated wires/cabling.

III. SUMMARY OF THE DISCLOSURE

According to an embodiment, a process of forming a polymeric material is disclosed. The process includes chemically reacting a polyvinyl chloride (PVC) material with a diamine to form a diamine-modified PVC material. The diamine has a chemical formula $(CH_2)_x(NH_2)_2$, where x is not less than 2. The process also includes chemically reacting a halogenated phthalate plasticizer with the diamine-modified PVC material to form a polymeric material having a phthalate plasticizer covalently bonded to a polymer chain.

According to another embodiment, a polymeric material is disclosed. The polymeric material has a phthalate plasticizer covalently bonded to a diamine-modified portion of a PVC polymer chain. The PVC polymer chain is modified using an aliphatic diamine. The aliphatic diamine has a chemical formula $(CH_2)_x(NH_2)_2$, where x is not less than 2.

According to another embodiment, a polymeric material is disclosed. The polymer material is formed by a process that includes chemically reacting a chlorinated polyvinyl chloride (CPVC) material with an aliphatic diamine to form a diamine-modified CPVC material. The aliphatic diamine has a chemical formula $(CH_2)_x(NH_2)_2$, where x is not less than 2. The process further includes chemically reacting a halogenated phthalate plasticizer with the diamine-modified CPVC material to form a polymeric material having a phthalate plasticizer covalently bonded to a polymer chain.

One advantage of the present disclosure is the ability to covalently bond a phthalate plasticizer to a polymer chain in order to reduce/prevent leach-out of plasticizer that may be associated with the use of polymeric materials having plasticizer additives in some applications. Another advantage of the present disclosure is the ability to improve freedom of movement of an aromatic group of the covalently bonded phthalate plasticizer by separating an aromatic portion of the phthalate plasticizer from a polymer backbone by at least two carbon atoms.

Features and other benefits that characterize embodiments are set forth in the claims annexed hereto and forming a further part hereof. However, for a better understanding of the embodiments, and of the advantages and objectives attained through their use, reference should be made to the Drawings and to the accompanying descriptive matter.

IV. BRIEF DESCRIPTION OF THE DRAWINGS

Figure 2:
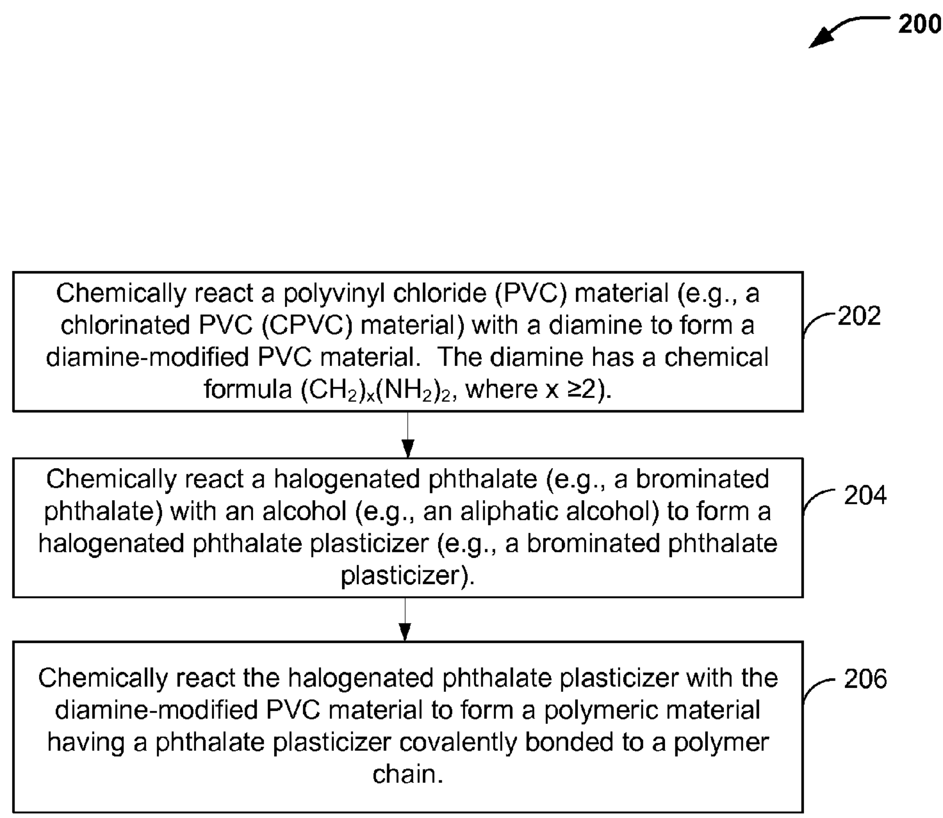

FIG. 1 is a chemical reaction diagram showing the preparation of a polymer material having a phthalate plasticizer covalently bonded to a polymer chain, according to one embodiment; and FIG. 2 is a flow diagram showing a particular embodiment of a process of preparing a polymeric material having a phthalate plasticizer covalently bonded to a polymer chain.

V. DETAILED DESCRIPTION

The present disclosure describes polymeric materials having phthalate plasticizers covalently bonded to a polymer chain and processes of producing such polymeric materials. In the present disclosure, a diamine having a chemical formula $(CH_2)_x(NH_2)_2$, where x is not less than 2, may be used to form a diamine-modified polymeric material (e.g., a diamine-modified PVC material). The diamine-modified polymeric material may be chemically reacted with a halogenated phthalate plasticizer (e.g., a brominated phthalate plasticizer) to form a polymer material having a phthalate plasticizer that is covalently bonded to a polymer chain. As described further herein, the use of a diamine having an alkyl chain length of at least 2 may allow for sufficient separation of an aromatic portion of the phthalate plasticizer from the polymer chain for freedom of movement (and associated plasticization benefits). Additionally, as described further herein, covalently bonding the phthalate plasticizer to the polymer chain may reduce/prevent leach-out of plasticizer in some applications.

Referring to FIG. 1, a chemical reaction diagram 100 illustrates the preparation of a polymeric material having a phthalate plasticizer covalently bonded to a polymer chain, according to one embodiment. In FIG. 1, three chemical reactions are illustrated. A first chemical reaction (illustrated at the bottom of FIG. 1) illustrates an example of a process of preparing a halogenated phthalate plasticizer. A second chemical reaction (illustrated at the top of FIG. 1) illustrates an example of a process of preparing a diamine-modified PVC material. A third chemical reaction (illustrated in the middle of FIG. 1) illustrates an example of covalently bonding a phthalate plasticizer to a polymer chain by chemically reacting the diamine-modified PVC material with the halogenated phthalate plasticizer. As described further herein, the use of a diamine having a chemical formula $(CH_2)_x(NH_2)_2$ (where x is not less than 2) to prepare the diamine-modified PVC material may allow for sufficient separation of the phthalate plasticizer from the polymer backbone to allow for freedom of movement of an aromatic group of the phthalate for plasticization of the PVC material. Further, covalently bonding the phthalate plasticizer to the PVC polymer chain may reduce/prevent leach-out of plasticizer in some applications (e.g., where the PVC material is used as an insulating material for wires/cables in immersion cooling applications).

The first chemical reaction (illustrated at the bottom of FIG. 1) is an illustrative, non-limiting example of a process of preparing a halogenated phthalate plasticizer via a chemical reaction of a halogenated phthalate with an alcohol. In the particular embodiment illustrated in FIG. 1, the halogenated phthalate plasticizer is a brominated phthalate plasticizer (e.g., brominated diisononyl phthalate (DINP)) that is formed via a chemical reaction of a brominated phthalate (e.g., 4-bromophthalic anhydride) with an aliphatic alcohol (e.g., isononyl alcohol). For illustrative purposes, FIG. 1 illustrates a ring-opening reaction of the brominated phthalic anhydride to bind a first isononyl group to the phathlate material, followed by a second isononyl group being bonded to the brominated phthalate material to form the brominated phthalate plasticizer.

In other embodiments, the halogenated phthalate may include an alternative halogen (e.g., Cl), the alcohol may include an alternative alcohol (or alcohols), or a combination thereof. As an illustrative, non-limiting example, the halogenated phthalate plasticizer may include brominated diisoheptyl phthalate (DIHP) that may be formed via a chemical reaction of 4-bromophthalic anhydride and isoheptyl alcohol. In some cases, the alcohol may be selected to have an alkyl chain length that is sufficient to provide a particular degree of plasticization in a polymeric material having the phthalate plasticizer covalently bonded to a polymer chain (as illustrated and further described herein with respect to the middle chemical reaction of FIG. 1). Thus, isononyl alcohol and isoheptyl alcohol are illustrative, non-limiting examples of aliphatic alcohols that may be used to prepare a halogenated phthalate plasticizer (e.g., brominated DINP or DIHP).

Prophetic Example

Preparation of Halogenated Phthalate Plasticizer

As a prophetic example, 4-bromophthalic anhydride (10 g) may be added to a 100 mL round bottom flask and stirred. Next, 1 equiv. of isononyl alcohol and a catalytic amount of sulfuric acid may be added. The mixture may then be heated to about 140° C. for about 6 hours. After about 6 hours, an additional 1 equiv. of isononyl alcohol may be added, and the mixture may be stirred for about another 6 hours. The reaction may then be cooled to room temperature, and the resulting brominated DINP product may be purified.

The second chemical reaction (illustrated at the top of FIG. 1) is an illustrative non-limiting example of a process of preparing a diamine-modified PVC material. In the example of FIG. 1, a portion of a PVC material is chlorinated, with the non-chlorinated portion of the PVC polymer chain represented by the integer m and the chlorinated portion of the PVC polymer chain represented by the integer n. It will be appreciated that a degree of chlorination of the PVC material may vary (e.g., based on a desired degree of plasticization for a particular PVC application). Further, an amount of diamine material that is chemically reacted with the CPVC material may vary (e.g., based on a degree of chlorination of the PVC material). As an illustrative, non-limiting example, an amount of plasticizer for a PVC material may be up to about 10 weight percent. In this case, a weight percentage of diamine that is reacted with the CPVC material may be slightly higher than a weight percentage of the plasticizer that is subsequently added. To illustrate, a weight percentage of diamine that is selected for chemical reaction with the CPVC material may be in a range of 5 to 20 weight percent, such as in a range of 5 to 10 weight percent, or in a range of 10 to 20 weight percent (depending on a desired amount of plasticizer in the final PVC material).

FIG. 1 illustrates that the CPVC material may be chemically reacted with a diamine having a chemical formula $(CH_2)_x(NH_2)_2$ to form a diamine-modified PVC material (where x is not less than 2). In the particular embodiment illustrated in FIG. 1, the diamine includes an aliphatic diamine (e.g., ethylene diamine). In other cases, alternative and/or additional diamines (e.g., aliphatic diamines) may be used to form the diamine-modified PVC material. As illustrative, non-limiting examples, the diamine may include ethylene diamine (where x=2) as shown in the example of FIG. 1, propylene diamine (where x=3), butylene diamine (where x=4), or a combination thereof (among other alternatives). As further described herein, having at least two carbon atoms separating the amine groups of the diamine may allow an aromatic group of the phthalate plasticizer to be sufficiently separated from the PVC backbone to allow for freedom of movement for alignment with polar/non-polar groups of the PVC/CPVC backbones for plasticization.

Prophetic Example

Formation of Amine-Modified PVC Material

As a prophetic example, chlorinated polyvinyl chloride (CPVC; 10 g) and THF (50 mL) may be added to a 100 mL round bottom flask and fitted to a mechanical stirrer. The mixture may be allowed to stir in order to dissolve the CPVC. Next, ethylenediamine (62.5 mL, 0.94 mol) may be dissolved in THF (100 mL). To the dissolved CPVC, ethylenediamine in THF (4 equiv to Cl) may be added. The mixture may then be allowed to stir for about 20 minutes. After reaction, the resulting polymer may be purified.

In the third chemical reaction (illustrated in the middle of FIG. 1), the diamine-modified PVC material may be chemically reacted with the halogenated phthalate plasticizer to form a polymeric material having a phthalate plasticizer covalently bonded to a polymer chain. Having at least two carbon atoms separating the amine groups of the diamine (e.g., 2 carbon atoms in the example of FIG. 1, where the diamine includes ethylene diamine) may allow for sufficient separation of an aromatic portion of the phthalate plasticizer from the PVC backbone for freedom of movement and associated plasticization benefits. Further, having the phthalate plasticizer covalently bonded to the PVC backbone may reduce/prevent leach-out of plasticizer material that may be associated with use of PVC materials in some applications. As an illustrative, non-limiting example, flexible PVC tubing may insulate cables/wires of information technology hardware. In the context of immersion cooling (e.g., using mineral oil as an immersion cooling fluid), covalently bonding the plasticizer to the PVC backbone may prevent plasticizer leach-out that may result from a plasticizer additive and mineral oil having similar solubility parameters.

Prophetic Example

Preparation of a Polymeric Material Having a Phthalate Plasticizer Covalently Bonded to a Polymer Chain As a prophetic example, to a 100 mL sealed reaction vessel, brominated DINP (25 g) and amine-modified CPVC (1.5 equiv.) may be added to THF (60 mL) along with a stir bar. Next, a palladium (II) tertiary phosphine complex catalyst (5 mol %) such as $L_2PdCl_2$ (L=tri-o-tolylphosphine) may be added along with LiHMDS (1.2 equiv.). LiHDMS is an abbreviation for lithium bis(trimethylsilyl)amide, which is a lithiated organosilicon compound with the formula $LiN(SiMe_3)_2$, with LiHDMS serving as a strong non-nucleophilic base and as a ligand. The reaction may then be heated to about 55° C. and held at about 55° C. for about 24 hours.

After reaction, the mixture may be cooled to room temperature, and the resulting product may be purified.

Thus, FIG. 1 illustrates an example of a process of preparing a polymer material having a phthalate plasticizer covalently bonded to a polymer chain. In the example of FIG. 1, a diamine having a chemical formula $(CH_2)_x(NH_2)_2$ (where x is not less than 2) is used to form a diamine-modified PVC material. Having at least two carbon atoms between the amine groups of the diamine may allow for sufficient movement of an aromatic portion of a phthalate plasticizer that is covalently bonded to the diamine-modified portion of the PVC polymer chain. Further, covalently bonding the phthalate plasticizer to the PVC backbone may prevent leach-out of the plasticizer that may be associated with use of additives for PVC plasticization in some applications (e.g., an immersion cooling application where mineral oil is used as an immersion cooling fluid).

FIG. 2 is a flow diagram of a particular embodiment of a process 200 of preparing a polymeric material having a phthalate plasticizer covalently bonded to a polymer chain. In the example of FIG. 2, the process 200 includes preparing a halogenated phthalate plasticizer using a halogenated phthalate and an alcohol. In some cases, one entity (e.g., a specialty chemical manufacturer) may prepare the halogenated phthalate plasticizer. In some cases, another entity (e.g., a plastics manufacturer) may utilize the halogenated phthalate plasticizer to prepare a polymeric material having the phthalate plasticizer covalently bonded to a polymer chain. In some cases, another entity (e.g., an insulated wire/casing manufacturer) may prepare an article of manufacture (e.g., a flexible PVC insulated wire/casing) using the polymeric material having the phthalate plasticizer covalently bonded to the polymer chain. Thus, the same entity or different entities may perform one or more operations of the process 200 illustrated in FIG. 2.

The process 200 includes chemically reacting a PVC material (e.g., a CPVC material) with a diamine to form a diamine-modified PVC material, at 202. The diamine has a chemical formula $(CH_2)_x(NH_2)_2$, where x is not less than 2. For example, referring to the chemical reaction illustrated at the top of FIG. 1, the CPVC material may be chemically reacted with the diamine (e.g., ethylene diamine, where x=2) to form the diamine-modified PVC material. As described further herein, in alternative embodiments, alternative and/or additional diamines may be used to form the diamine-modified PVC material.

In the particular embodiment illustrated in FIG. 2, the process 200 includes chemically reacting a halogenated phthalate with an alcohol to form a halogenated phthalate plasticizer, at 204. For example, referring to the chemical reaction illustrated at the bottom of FIG. 1, the halogenated phthalate (e.g., a brominated phthalate, such as 4-bromophthalic anhydride) may be chemically reacted with the alcohol (e.g., an aliphatic alcohol, such as isononyl alcohol) to form the halogenated phthalate plasticizer (e.g., a brominated phthalate plasticizer, such as DINP). As described further herein, alternative phthalate(s) and/or alcohol(s) may be used to form alternative halogenated phthalate plasticizers. As an illustrative, non-limiting example, a brominated diisoheptyl phthalate (DIHP) plasticizer may be formed by chemically reacting 4-bromophthalic anhydride with isoheptyl alcohol.

The process 200 includes chemically reacting the halogenated phthalate plasticizer with the diamine-modified PVC material to form a polymeric material having a phthalate plasticizer covalently bonded to a polymer chain, at 206. For example, referring to the chemical reaction illustrated in the middle of FIG. 1, the diamine-modified PVC material (e.g., ethylene diamine modified PVC material) may be chemically reacted with the halogenated phthalate plasticizer (e.g., brominated DINP) to form the polymeric material having the phthalate plasticizer (e.g., DINP) covalently bonded to the PVC polymer chain.

Thus, FIG. 2 illustrates an example of a process of forming a polymeric material (e.g., a PVC material) having a phthalate plasticizer covalently bonded to a polymer chain (e.g., a PVC polymer chain). As described further herein, having at least two carbon atoms separating the amine groups of the diamine that is used to form the diamine-modified PVC material may allow an aromatic portion of the phthalate plasticizer to have sufficient freedom of movement for plasticization of the PVC material. Further, in some applications (e.g., immersion cooling), covalently bonding the phthalate plasticizer to the PVC polymer chain may prevent leach-out of plasticizer material that may result from solubility parameter similarity.

The previous description of the disclosed embodiments is provided to enable any person skilled in the art to make or use the disclosed embodiments. Various modifications to these embodiments will be readily apparent to those skilled in the art, and the generic principles defined herein may be applied to other embodiments without departing from the scope of the disclosure. Thus, the present disclosure is not intended to be limited to the embodiments shown herein but is to be accorded the widest scope possible consistent with the principles and features as defined by the following claims.

The invention claimed is:

1. A process of forming a polymeric material, the process comprising:

chemically reacting a polyvinyl chloride (PVC) material with a diamine having a chemical formula $(CH_2)_x(NH_2)_2$ to form a diamine-modified PVC material, wherein x is not less than 2; and chemically reacting a halogenated phthalate plasticizer with the diamine-modified PVC material to form a polymeric material having a phthalate plasticizer covalently bonded to a polymer chain.

2. The process of claim 1, wherein the PVC material includes a chlorinated PVC (CPVC) material.

3. The process of claim 1, wherein the diamine includes ethylene diamine.

4. The process of claim 1, wherein the halogenated phthalate plasticizer includes a brominated phthalate.

5. The process of claim 4, wherein the brominated phthalate includes 4-bromophthalic anhydride.

6. The process of claim 1, further comprising chemically reacting a halogenated phthalate with an alcohol to form the halogenated phthalate plasticizer.

7. The process of claim 6, wherein the alcohol includes an aliphatic alcohol.

8. The process of claim 7, wherein the aliphatic alcohol includes isononyl alcohol.

9. The process of claim 8, wherein the halogenated phthalate plasticizer includes brominated diisononyl phthalate (DINP).

10. The process of claim 7, wherein the aliphatic alcohol includes isoheptyl alcohol.

11. The process of claim 10, wherein the halogenated phthalate plasticizer includes brominated diisoheptyl phthalate (DIHP).

12. A polymeric material having a phthalate plasticizer covalently bonded to a diamine-modified portion of a polyvinyl chloride (PVC) polymer chain, wherein the PVC polymer chain is modified using an aliphatic diamine having a chemical formula $(CH_2)_x(NH_2)_2$, wherein x is not less than 2.

13. The polymeric material of claim 12, wherein the phthalate plasticizer includes diisononyl phthalate (DINP).

14. The polymeric material of claim 12, wherein the phthalate plasticizer includes diisoheptyl phthalate (DIHP).

15. The polymeric material of claim 12, wherein the aliphatic diamine includes ethylene diamine.

16. A polymeric material formed by a process comprising:

chemically reacting a chlorinated polyvinyl chloride (CPVC) material with an aliphatic diamine having a chemical formula $(CH_2)_x(NH_2)_2$ to form a diamine-modified CPVC material, wherein x is not less than 2; and chemically reacting a halogenated phthalate plasticizer with the diamine-modified CPVC material to form a polymeric material having a phthalate plasticizer covalently bonded to a polymer chain.

17. The polymeric material of claim 16, wherein the halogenated phthalate plasticizer includes a brominated phthalate plasticizer.

18. The polymeric material of claim 17, wherein the brominated phthalate plasticizer includes brominated diisononyl phthalate (DINP).

19. The polymeric material of claim 17, wherein the brominated phthalate plasticizer includes brominated diisoheptyl phthalate (DIHP).

20. The polymeric material of claim 16, wherein the aliphatic diamine includes ethylene diamine.

* * * * *